(12) United States Patent
Kwon et al.

(10) Patent No.: US 9,995,731 B2
(45) Date of Patent: Jun. 12, 2018

(54) CONSTRUCTION OF MITOCHONDRIAL UQCRB MUTANT EXPRESSING CELLS AND UTILIZATION OF THE CELLS FOR UQCRB ASSAY SYSTEM THEREOF

(71) Applicant: INDUSTRY-ACADEMIC COOPERATION FOUNDATION, YONSEI UNIVERSITY, Seoul (KR)

(72) Inventors: Ho Jeong Kwon, Seoul (KR); Jung Hwa Chang, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 298 days.

(21) Appl. No.: 14/705,529

(22) Filed: May 6, 2015

(65) Prior Publication Data
US 2016/0103120 A1    Apr. 14, 2016

(30) Foreign Application Priority Data
Oct. 14, 2014  (KR) .......................... 10-2014-0138428

(51) Int. Cl.
*G01N 33/567*  (2006.01)
*G01N 33/50*   (2006.01)
*C12N 9/02*    (2006.01)

(52) U.S. Cl.
CPC ....... *G01N 33/5011* (2013.01); *C12N 9/0055* (2013.01); *C12Y 110/02002* (2013.01); *G01N 2333/90219* (2013.01); *G01N 2800/7014* (2013.01)

(58) Field of Classification Search
None
See application file for complete search history.

(56) References Cited

U.S. PATENT DOCUMENTS

2006/0127902 A1    6/2006   Madden et al.

FOREIGN PATENT DOCUMENTS

WO    WO-2011/113819 A2    9/2011

OTHER PUBLICATIONS

Chang et al in "A mutation in the mitochondrial protein UQCRB promotes angiogenesis through the generation of mitochondrial reactive oxygen species" (Biochemical and Biophysical Research Communications vol. 455, available online Nov. 11, 2014: pp. 290-297).*

* cited by examiner

*Primary Examiner* — Catherine S Hibbert
(74) *Attorney, Agent, or Firm* — Clark & Elbing LLP; Susan M. Michaud

(57) ABSTRACT

The present invention relates to a mitochondrial UQCRB mutant cell line expressing the UQCRB mutant protein. The present invention is directed to a novel research method for UQCRB activity evaluation using a novel mitochondrial UQCRB mutant cell line, and provides a method for anti-cancer activity evaluation, a method for angiogenesis inhibitory activity evaluation, and a method for screening a UQCRB activity inhibitor. In particular, the cell line of the present invention is a novel cell line having cell proliferative and angiogenesis inducing activities, and provides a method for screening an angiogenesis inhibitor or an anticancer material through the UQCRB activity inhibitory mechanism, and thus can be applied in the development of therapeutic agents against angiogenesis or mitochondria-mediated diseases and various cancers.

7 Claims, 11 Drawing Sheets

SEQUENCE LISTING

<160> NUMBER OF SEQ ID NOS: 19

<210> SEQ ID NO 1
<211> LENGTH: 125
<212> TYPE: PRT
<213> ORGANISM: Artificial Sequence
<220> FEATURE:
<223> OTHER INFORMATION: Synthetic Construct

<400> SEQUENCE: 1

Met Ala Gly Lys Gln Ala Val Ser Ala Ser Gly Lys Trp Leu Asp Gly
1               5                   10                  15

Ile Arg Lys Trp Tyr Tyr Asn Ala Ala Gly Phe Asn Lys Leu Gly Leu
            20                  25                  30

Met Arg Asp Asp Thr Ile Tyr Glu Asp Glu Asp Val Lys Glu Ala Ile
        35                  40                  45

Arg Arg Leu Pro Glu Asn Leu Tyr Asn Asp Arg Met Phe Arg Ile Lys
    50                  55                  60

Arg Ala Leu Asp Leu Asn Leu Lys His Gln Ile Leu Pro Lys Glu Gln
65                  70                  75                  80

Trp Thr Lys Tyr Glu Glu Asn Phe Tyr Leu Glu Pro Tyr Leu Lys
                85                  90                  95

Glu Val Ile Arg Glu Arg Lys Glu Lys Asn Gly Gln Arg Ser Asn His
                100                 105                 110

Val Val Glu Val Cys Gly Cys Ser Cys Tyr Glu Asp Gly
            115                 120                 125

<210> SEQ ID NO 2
<211> LENGTH: 375
<212> TYPE: DNA
<213> ORGANISM: Artificial Sequence
<220> FEATURE:
<223> OTHER INFORMATION: Synthetic Construct

<400> SEQUENCE: 2
atggctggta agcaggccgt ttcagcatca ggcaagtggc tggatggtat tcgaaaatgg      60
tattacaatg ctgcaggatt caataaactg gggttaatgc gagatgatac aatatacgag     120
gatgaagatg taaagaagc cataagaaga cttcctgaga accttttataa tgacaggatg     180 tttcgcatta gagggcact ggacctgaac ttgaagcatc agatcttgcc taaagagcag     240
tggaccaaat atgaagagga aaatttctac cttgaaccgt atctgaaaga ggttattcgg     300
gaaagaaaag aaaagaacgg ccagcgcagc aaccacgtgg tggaggtgtg cggctgcagc     360
tgctacgagg acggc                                                     375

<210> SEQ ID NO 3
<211> LENGTH: 111
<212> TYPE: PRT
<213> ORGANISM: Artificial Sequence
<220> FEATURE:
<223> OTHER INFORMATION: Synthetic Construct

<400> SEQUENCE: 3

Met Ala Gly Lys Gln Ala Val Ser Ala Ser Gly Lys Trp Leu Asp Gly
1               5                   10                  15

Ile Arg Lys Trp Tyr Tyr Asn Ala Ala Gly Phe Asn Lys Leu Gly Leu
            20                  25                  30

Met Arg Asp Asp Thr Ile Tyr Glu Asp Glu Asp Val Lys Glu Ala Ile
        35                  40                  45

```
Arg Arg Leu Pro Glu Asn Leu Tyr Asn Asp Arg Met Phe Arg Ile Lys
     50                  55                  60
Arg Ala Leu Asp Leu Asn Leu Lys His Gln Ile Leu Pro Lys Glu Gln
 65                  70                  75                  80
Trp Thr Lys Tyr Glu Glu Glu Asn Phe Tyr Leu Glu Pro Tyr Leu Lys
                 85                  90                  95
Glu Val Ile Arg Glu Arg Lys Glu Arg Glu Glu Trp Ala Lys Lys
                100                 105                 110
```

<210> SEQ ID NO 4
<211> LENGTH: 27
<212> TYPE: DNA
<213> ORGANISM: Artificial Sequence
<220> FEATURE:
<223> OTHER INFORMATION: Synthetic Construct

<400> SEQUENCE: 4
atgtgaattc atggctggta agcaggc                                27

<210> SEQ ID NO 5
<211> LENGTH: 87
<212> TYPE: DNA
<213> ORGANISM: Artificial Sequence
<220> FEATURE:
<223> OTHER INFORMATION: Synthetic Construct

<400> SEQUENCE: 5
ctcgaggccg tcctcgtagc agctgcagcc gcacacctcc accacgtggt tgctgcgctg    60
gccgttcttt tcttttcttt cccgaat                                87

<210> SEQ ID NO 6
<211> LENGTH: 28
<212> TYPE: DNA
<213> ORGANISM: Artificial Sequence
<220> FEATURE:
<223> OTHER INFORMATION: Synthetic Construct

<400> SEQUENCE: 6
atgtgaattc atggctggta agcaggcc                               28

<210> SEQ ID NO 7
<211> LENGTH: 28
<212> TYPE: DNA
<213> ORGANISM: Artificial Sequence
<220> FEATURE:
<223> OTHER INFORMATION: Synthetic Construct

<400> SEQUENCE: 7
atgcctcgag cttctttgcc cattcttc                               28

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
gctggcccca gccgctggag                                        20

<210> SEQ ID NO 9
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 9
gagtgcaggg tcagcactac                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
acccatggca gaaggaggag                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gacaccagag tccgacccgg                                               20

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Gly Ala Pro Asp His
1               5

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
aacagcgaca cccactcctc                                               20

<210> SEQ ID NO 14
<211> LENGTH: 21
<212> TYPE: DNA
<213> ORGANISM: Artificial Sequence
<220> FEATURE:
<223> OTHER INFORMATION: Synthetic Construct

<400> SEQUENCE: 14
ggagggagaa ttcagtgtgg t                                             21

<210> SEQ ID NO 15
<211> LENGTH: 375
<212> TYPE: DNA
<213> ORGANISM: Artificial Sequence
<220> FEATURE:
<223> OTHER INFORMATION: Synthetic Construct

<400> SEQUENCE: 15
atggctggta agcaggccgt ttcagcatca ggcaagtggc tggatggtat tcgaaaatgg    60
```

```
tattacaatg ctgcaggatt caataaactg gggttaatgc gagatgatac aatatacgag      120
gatgaagatg taaagaagc cataagaaga cttcctgaga acctttataa tgacaggatg      180
tttcgcatta agagggcact ggacctgaac ttgaagcatc agatcttgcc taaagagcag     240
tggaccaaat atgaagagga aaatttctac cttgaaccgt atctgaaaga ggttattcgg     300
gaaagaaaag aaagaacgg ccagcgcagc aaccacgtgg tggaggtgtg cggctgcagc     360
tgctacgagg acggc                                                     375
```

```
<210> SEQ ID NO 16
<211> LENGTH: 333
<212> TYPE: DNA
<213> ORGANISM: Homo sapiens

<400> SEQUENCE: 16
atggctggta agcaggccgt ttcagcatca ggcaagtggc tggatggtat tcgaaaatgg     60
tattacaatg ctgcaggatt caataaactg gggttaatgc gagatgatac aatatacgag    120
gatgaagatg taaagaagc cataagaaga cttcctgaga acctttataa tgacaggatg    180
tttcgcatta agagggcact ggacctgaac ttgaagcatc agatcttgcc taaagagcag   240
tggaccaaat atgaagagga aaatttctac cttgaaccgt atctgaaaga ggttattcgg   300
gaaagaaaag aaagagaaga atgggcaaag aag                                333
```

```
<210> SEQ ID NO 17
<211> LENGTH: 4
<212> TYPE: PRT
<213> ORGANISM: Artificial Sequence
<220> FEATURE:
<223> OTHER INFORMATION: Synthetic Construct

<400> SEQUENCE: 17

Ala Ala Ala Ala
1
```

```
<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Arg Glu Glu Trp Ala Lys Lys
1               5
```

```
<210> SEQ ID NO 19
<211> LENGTH: 21
<212> TYPE: PRT
<213> ORGANISM: Artificial Sequence
<220> FEATURE:
<223> OTHER INFORMATION: Synthetic Construct

<400> SEQUENCE: 19

Lys Asn Gly Gln Arg Ser Asn His Val Val Glu Val Cys Gly Cys Ser
1               5                  10                  15

Cys Tyr Glu Asp Gly
            20
```

CONSTRUCTION OF MITOCHONDRIAL UQCRB MUTANT EXPRESSING CELLS AND UTILIZATION OF THE CELLS FOR UQCRB ASSAY SYSTEM THEREOF

BACKGROUND OF THE INVENTION

Field of the Invention

The present invention relates to construction of mitochondrial UQCRB mutant expressing cells and utilization of the cells for UQCRB assay system thereof.

Description of the Prior Art

The electron transport chain (ETC) of mitochondria consists of five complexes and plays a crucial rule in energy production by ATP synthesis [1]. There have been numerous studies associated with the roles of various mitochondrial proteins in multiple diseases such as metabolic diseases and cancers [1,2,3,4]. However, information about the relationship between complex III and angiogenesis is limited.

Ubiquinol-cytochrome c reductase binding protein (UQCRB), which is a nuclear-encoded 13.4-kDa subunit of complex III, has been shown to function in association with the electron transport and the maintenance of complex III [5]. Recently, the potential role of UQCRB in angiogenesis has been demonstrated by identifying it as a target of the natural anti-angiogenesis inhibitor terpestacin [6]. UQCRB is involved in mitochondrial reactive oxygen species (mROS)- and hypoxia-inducible factor (HIF)-mediated angiogenesis by modulating the oxygen-sensing mechanism that regulates hypoxia responses. Moreover, UQCRB regulates vascular endothelial growth factor receptor 2 (VEGFR2)-signaling-induced angiogenesis [7]. Recent studies have demonstrated that the genetic variations of UQCRB were observed in several cancers, including hepatocellular carcinoma [8], ovarian cancer [9], pancreatic ductal adenocarcinoma [10], and colorectal cancer [11]. This potential of UQCRB to cause disease indicates its important role in angiogenesis and other mitochondria-mediated disorders.

In a recent report on the hereditary defects of the UQCRB gene, a Turkish girl with UQCRB and isolated complex III defects showed hypoglycemia and lactic acidosis during a metabolic crisis in her babyhood, but had normal growth in her childhood [2]. Based on this result, the present inventors constructed UQCRB mutant stable cell lines MT1 and MT2 and investigated their biological functions in angiogenesis. Notably, MT1 and MT2 showed remarkably increased growth and pro-angiogenic activities, together with mitochondrial structural abnormalities. Conversely, the cell proliferation of UQCRB mutants was significantly decreased by treatment with the UQCRB inhibitors terpestacin and A1938.

In summary, these results suggest that UQCRB and its mutation play a key role in angiogenesis and that UQCRB mutants could be useful tools for exploring the functions of UQCRB in human cells.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have endeavored to search the roles of UQCRB and a mutant thereof in angiogenesis and cell proliferative diseases. As a result, the UQCRB mutant cell lines were newly constructed, and then the UQCRB mutant cell line was verified to exhibit angiogenesis and increased cell proliferation. In addition, the increased cell proliferation was verified to be inhibited by treatment with a UQCRB inhibitor, and thus the present UQCRB mutant cell line is newly provided as a novel cell line for evaluating UQCRB activity.

Accordingly, an aspect of the present invention is to provide a mitochondrial ubiquinol-cytochrome c reductase binding protein (UQCRB) mutant animal cell line expressing a UQCRB mutant protein.

Another aspect of the present invention is to provide a method for anticancer activity evaluation.

Another aspect of the present invention is to provide a method for angiogenesis inhibitory activity evaluation.

Another aspect of the present invention is to provide a method for screening a UQCRB activity inhibitor.

Other purposes and advantages of the present disclosure will become clarified by the following detailed description of the invention, claims, and drawings.

Technical Solution

In accordance with an aspect of the present invention, there is provided a mitochondrial ubiquinol-cytochrome c reductase binding protein (UQCRB) mutant animal cell line expressing a UQCRB mutant protein.

The present inventors have endeavored to search the roles of UQCRB and a mutant thereof in angiogenesis and cell proliferative diseases. As a result, the UQCRB mutant cell lines were newly constructed, and then the UQCRB mutant cell line was verified to exhibit angiogenesis and increased cell proliferation. In addition, the increased cell proliferation was verified to be inhibited by treatment with a UQCRB inhibitor, and thus the present UQCRB mutant cell line is newly provided as a novel cell line for evaluating UQCRB activity.

Ubiquinol-cytochrome c reductase binding protein (UQCRB) is one of the subunits of mitochondrial complex III and is a target protein of the natural anti-angiogenic small molecule terpestacin. Previously, the biological role of UQCRB was thought to be limited to the maintenance of complex III. However, the identification and validation of UQCRB as a target protein of terpestacin enabled the role of UQCRB in oxygen sensing and angiogenesis to be elucidated. To explore the biological role of this protein further, UQCRB mutant stable cell lines were generated on the basis of a human case report. We demonstrated that these cell lines exhibited pro-angiogenic activity via mitochondrial reactive oxygen species (mROS)-mediated HIF1 signal transduction. Furthermore, a morphological abnormality in mitochondria was detected in UQCRB mutant stable cell lines. In addition, the proliferative effect of the UQCRB mutants was significantly regulated by the UQCRB inhibitors terpestacin and A1938. Collectively, these results provide a molecular basis for UQCRB-related biological processes and reveal potential key roles of UQCRB in angiogenesis and mitochondria-mediated metabolic disorders.

Therefore, the present inventors have constructed a mitochondrial UQCRB mutant cell line for exploring the mechanism of UQCRB in angiogenesis and mitochondria-mediated metabolic diseases or cancers, and attempt to suggest novel research methods for the evaluation of UQCRB activity using the mitochondrial UQCRB mutant cell line.

As used herein, the term "mutation" refers to a change in the nucleotide sequence coding UQCRB through substitution, insertion, deletion, or a combination thereof. For example, the deletion of a gene and the insertion of heterologous sequence into the gene may cause truncation, nonsense mutation, frameshift mutation, and missense mutation of the gene. These specific mutations of the gene may be performed by methods established in the art.

Meanwhile, the deletion of a nucleotide sequence may be performed by various mutagenesis methods known in the art. For instance, the deletion of the UQCRB coding sequence may be performed by PCR mutagenesis method or cassette mutagenesis method (Sambrook, J. et al., *Molecular Cloning. A Laboratory Manual,* 3rd ed. Cold Spring Harbor Press (2001)).

According to the present invention, the animal cell line of the present invention is a mitochondrial UQCRB mutant animal cell line, which is transfected with a vector including a nucleotide sequence coding human ubiquinol-cytochrome c reductase binding protein (UQCRB) mutant represented by SEQ ID NO: 1, to express the human UQCRB protein.

The vector used herein includes an expression construct including a ubiquinol-cytochrome c reductase binding protein (UQCRB)-coding nucleotide sequence. The expression construct includes "a promoter operating in animal cells—a UQCRB coding nucleotide sequence—a polyadenylation sequence". Herein, the human UQCRB mutant represented by SEQ ID NO: 1 is substantially a polypeptide obtained by the mutation of the amino acid sequence of the human UQCRB, and has a 4-bp deletion at nucleotides 338-341 of the nucleotide sequence of the human UQCRB gene (Accession number: NM_006294). That is, the protein product of the UQCRB mutant sequence of the present invention has alterations in seven amino acid residues and an additional stretch of 14 amino acids at the C-terminal end (see FIG. 1A).

The UQCRB mutant of the present invention is a target protein of the anti-angiogenic small molecule terpestacin. More specifically, UQCRB is encoded in the nucleus, and plays a key role in constructing and maintaining the complex III structure. The present inventors have elucidated that the expression of the UQCRB mutant protein induces the mitochondrial reactive oxygen species (mROS) generation and stabilizes HIF-1α, thereby exhibiting angiogenic and cell proliferative effects.

In order to efficiently express the UQCRB mutant protein of the present invention, the UQCRB-coding nucleotide sequence preferably exists in an appropriate expression construct. In the expression construct, the UQCRB-coding nucleotide sequence is preferably operatively linked to the promoter.

The expression construct of the present invention can be constructed through various methods known in the art, and a specific method thereof is disclosed in Sambrook et al., *Molecular Cloning, A Laboratory Manual,* Cold Spring Harbor Laboratory Press (2001), which is incorporated herein by reference.

According to the present invention, the amino acid sequence of the human UQCRB mutant is represented by SEQ ID NO: 1, and the nucleotide sequence of UQCRB is represented by SEQ ID NO: 2. Meanwhile, the transfected animal cell line of the present invention expresses the human UQCRB mutant protein continuously and stably.

As used herein, the term "nucleotide" has a meaning including DNA and RNA molecules, and includes natural occurring nucleotides and analogues with modified sugars or bases (Scheit, *Nucleotide Analogs,* John Wiley, New York (1980); Uhlman and Peyman, *Chemical Reviews,* 90:543-584(1990)).

In the vector of the present invention, the human ubiquinol-cytochrome c reductase binding protein (UQCRB)-coding nucleotide sequence includes a nucleotide sequence showing substantial identity to the nucleotide sequence represented by SEQ ID NO: 2. The term "substantial identity" means that, when the present nucleotide sequence and another nucleotide sequence are aligned to correspond to each other as much as possible and the aligned sequences are analyzed using an algorithm that is normally used in the art, the present nucleotide sequence has at least 80% sequence identity, preferably at least 90%, most preferably at least 95% sequence identity compared to another nucleotide sequence.

As used herein, the term "promoter" refers to a DNA sequence that regulates the expression of a coding sequence or functional RNA. The expression vector of the present invention is a recombinant expression vector, and a material to be expressed-coding nucleotide sequence is operatively linked to the promoter. As used herein, the term "operatively linked" refers to a functional linkage between a nucleic acid expression regulating sequence (e.g., a promoter sequence, a signal sequence, or an array at the binding site of a transcription control factor) and the another nucleic acid sequence, and the regulating sequence regulates the transcription and/or translation of the other nucleic acid sequence.

The promoter is operable in animal cells, including CMV (Cytomegalovirus) promoter, the adenovirus late promoter, the vaccinia virus 7.5K promoter, SV40 (Simian Virus 40) promoter, SV40E1 promoter, HSV (Herpes simplex virus) tk promoter, RSV (Respiratory syncytial virus) promoter, EF1 (elongation factor-1) alpha promoter, metallothionein promoter, beta-actin promoter, human IL-2 (interleukin-2) gene promoter, human IFN (interferon) gene promoter, human IL-4 gene promoter, human lymphotoxin gene promoter and human GM-CSF (Granulocyte macrophage colony-stimulating factor) gene promoter.

Herein, the vector includes a polyadenylation sequence as a transcription termination sequence, and the polyadenylation sequence is preferably a bovine growth hormone terminator, herpes simplex virus (HSV)-derived thymidine kinase (TK), or a simian virus 40 (SV40)-derived polyadenylation sequence.

The vector used herein may include, as a selective marker, an antibiotic-resistant gene acting on animal cells, which is normally used in the art, and for example, may include genes resistant to Geneticin (G418), puromycin, ampicillin, gentamicin, carbenicillin, chloramphenicol, streptomycin, kanamycin, neomycin, and tetracycline.

The vector, including the human UQCRB mutant coding nucleotide sequence used herein, is operated to transfect animal cells. Examples of the animal cells used herein may include mammalian, rodent, bird, and insect cells. According to the present invention, the animal cells are mammalian cells.

When the expression vectors of the present invention are introduced to manufacture transfected animal cells, the vectors may be introduced into cells by microinjection (Capecchi, M. R., Cell, 22:479(1980) and Harland and Weintraub, J. Cell Biol. 101:1094-1099(1985)), calcium phosphate co-precipitation (Graham, F. L. et al., Virology, 52:456(1973) and Chen and Okayama, Mol. Cell. Biol. 7:2745-2752(1987)), electroporation (Neumann, E. et al., EMBO J., 1:841(1982) and Tur-Kaspa et al., Mol. Cell Biol., 6:716-718(1986)), liposome-mediated transfection (Wong, T. K. et al., Gene, 10:87(1980) and Nicolau and Sene, Biochim. Biophys. Acta, 721:185-190(1982); and Nicolau et al., Methods Enzymol., 149:157-176(1987)), DEAE-dextran treatment (Gopal, Mol. Cell Biol., 5:1188-1190(1985)) and particle bombardment (Yang et al., Proc. Natl. Acad. Sci., 87:9568-9572(1990)).

The transformed animal cells can be maintained in culture media, such as Eagles's MEM (Eagle's minimum essential medium), α-MEM, Iscove's MEM, CMRL 1066, RPMI 1640, F12, F10, DMEM (Dulbecco's modification of Eagle's medium), Way-mouth's MB752/1, McCoy's 5A or MCDB series, preferably, DMEM.

According to another aspect of the present invention, the present invention provides a method for anticancer activity evaluation, the method comprising:

(a) establishing a mitochondrial ubiquinol-cytochrome c reductase binding protein (UQCRB) mutant animal cell line expressing a UQCRB mutant protein;

(b) contacting a test substance with the animal cells; and (c) analyzing the anticancer activity of the test substance.

The method for anticancer activity evaluation of the present invention is performed by analyzing anticancer activity of test substances, and may be used as the same meaning as the screening method of anticancer materials. Meanwhile, the method for anticancer activity evaluation of the present invention uses the foregoing mitochondrial UQCRB mutant animal cell line of the present invention, and thus descriptions of overlapping contents therebetween are omitted to avoid excessive complication of the specification due to repetitive descriptions thereof.

According to the present invention, the anticancer activity evaluation may be performed by analyzing the UQCRB inhibitory activity of the test substances. That is, in step (c), if the UQCRB activity is inhibited by the test substance, the test substance is determined to have anticancer activity.

The present invention will be described in detail by steps.

Step (a): Establishment of Mitochondrial UQCRB Mutant Animal Cell Line

First, a mitochondrial UQCRB mutant cell line expressing a UQCRB mutant protein is established. According to the present invention, the cell line expresses the UQCRB mutant protein in which the mitochondrial UQCRB-coding nucleotide sequence is mutated through substitution, insertion, deletion, or a combination thereof. More specifically, the UQCRB mutant cell line is transfected with an expression vector including a nucleotide sequence coding a human ubiquinol-cytochrome c reductase binding protein (UQCRB) mutant represented by SEQ ID NO: 1.

Herein, the foregoing expression vector of the present invention is operated to transfect animal cells. According to the present invention, the animal cells are mammal cells.

The transformed animal cells can be maintained in culture media, such as Eagles's MEM, α-MEM, Iscove's MEM, CMRL 1066, RPMI 1640, F12, F10, DMEM, Way-mouth's MB752/1, McCoy's 5A or MCDB series, preferably, DMEM.

Step (b): Contact Between Transfected Animal Cells and Test Substance

Then, the transfected animal cells are contacted with a test substance. The test substance is contacted with the transfected animal cells, thereby affecting the signal transduction associated with cell proliferation and angiogenesis (e.g., Mros-mediated or HIF-1α-mediated angiogenesis signaling and cell proliferation signaling).

The contact may be performed in vitro or in vivo, and for example, the transfected animal cells and the test substance may be combined in vitro (e.g., on a cell culture plate) in cases where the method is an in vitro assay, and the contact between the transfected animal cells and the test substance may be induced by administering the test substance into in vivo subjects including the transfected animals in cases where the method is an in vivo assay.

The test substance is one contain chemicals, nucleotides, antisense-RNA, siRNA (small interference RNA), miRNA, peptide, protein, antibody and natural extracts, but not limited to.

In cases where the test substance to be analyzed by the method for anticancer activity evaluation of the present invention is a compound, the compound may be a single compound or a mixture of compounds (e.g., a natural extract or a cell or tissue cultured material). The test substance may be obtained from a library of synthetic or natural compounds. The method of obtaining the library of such compounds is known in the art. Synthetic compound libraries are and commercially available from Maybridge Chemical Co. (UK), Comgenex (USA), Brandon Associates (USA), Microsource (USA) and Sigma-Aldrich (USA), and libraries of natural compounds are commercially available from Pan Laboratories (USA) and MycoSearch (USA).

The test substance may be obtained through various known combinational library methods known in the art. For example, it may be obtained by a biological library method, a spatially-addressable parallel solid phase or solution phase library method, a synthetic library method requiring deconvolution, a "one-bead one-compound" library method, and a synthetic library method using affinity chromatography selection. The synthesis of molecular libraries, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994 or the like is disclosed.

Step (c): Analysis of Anticancer Activity of Test Substance

Finally, the anticancer activity of the test substance on the transfected animal cells is analyzed. The anticancer activity analysis may be performed by assay methods using various known anticancer-related molecular mechanisms, and may be performed by analyzing, for example, gene transcript expression, protein expression, binding between proteins, cell migration, cell invasion, or the like.

The gene transcript expression may be analyzed by polymerase chain reaction (PCR), reverse transcription (RT)-PCR, real-time PCR, or microarray assay; the protein expression may be analyzed by western blotting, fluorescence microscopy, or the like; and the binding between protein may be analyzed by ELISA, fluorescence microscopy, yeast-two hybrid assay.

The test substance may be labeled by a substance (e.g., dye) generating a detectable signal, such as, but not limited to, chemical (e.g., biotin), enzymetic (e.g., horseradish peroxidase, alkaline phosphatase, peroxidase, luciferase, beta-galactosidase and beta-glucosidase), radio-isotope (e.g., $C^{14}$, $I^{125}$, $P^{32}$ and $S^{35}$), fluorescent [coumarin, fluoresin, FITC (fluoresein Isothiocyanate), rhodamine 6G, rhodamine B, TAMRA (6-carboxy-tetramethyl-rhodamine), Cy-3, Cy-5, Texas Red, Alexa Fluor, DAPI (4,6-diamidino-2-phenylindole), HEX, TET, Dabsyl and FAM], luminescent, chemiluminescent and FRET (fluorescence resonance energy transfer) or metallic substances (gold and silver).

In cases where the detectable label is a labeled test substance, the intercellular locus of the test substance or whether the test substance binds to a specific protein can be analyzed by detecting a signal generated from the label. For example, in cases where alkaline phosphatase is used as a label, the signal is detected using color reaction substrates, such as bromo-chloro-indolyl phosphate (BCIP), nitroblue tetrazolium (NBT), naphthol-AS-B1-phosphate, and enhanced chemifluorescence (ECF). In cases where horseradish peroxidase is used as a label, the signal is detected using substrates, such as chloronaphthol, aminoethyl carbazole, diaminobenzidine, D-luciferin, lucigenin (bis-n-methylacridinium nitrate), Resorufin benzyl ether, luminol, Amplex Red reagent (10-acetyl-3,7-dihydroxyphenoxazine), HYR (p-phenylenediamine-HCl and pyrocatechol), tetramethylbenzidine (TMB), 2,2'-Azine-di[3-ethylbenzthiazoline sulfonate] (ABTS), o-phenylenediamine (OPD), and naphtol/pyronin.

According to another aspect of the present invention, the present invention provides a method for angiogenesis inhibitory activity evaluation, the method comprising:

(a) establishing a mitochondrial ubiquinol-cytochrome c reductase binding protein (UQCRB) mutant animal cell line expressing a UQCRB mutant protein;

(b) contacting a test substance with the animal cells; and (c) analyzing the angiogenesis inhibitory activity of the test substance.

The method for angiogenesis inhibitory activity evaluation of the present invention is performed by analyzing angiogenic activity of a test substance, and may be used as the same meaning as the screening method of angiogenesis inhibitors. Meanwhile, the method for angiogenesis inhibitory activity evaluation of the present invention uses the foregoing mitochondrial UQCRB mutant animal cell line of the present invention, and thus descriptions of overlapping contents therebetween are omitted to avoid excessive complication of the specification due to repetitive descriptions thereof.

According to the present invention, the angiogenesis inhibitory activity evaluation may be performed by analyzing the UQCRB inhibitory activity of the test substance. That is, if the UQCRB activity is inhibited by the test substance in step (c), the test substance is determined to have angiogenesis inhibitory activity.

The angiogenesis inhibitory activity may be evaluated by measuring mitochondrial reactive oxygen species (mROS)-mediated or HIF-1α-mediated angiogenic activity, and more specifically, may be evaluated by measuring mitochondrial reactive oxygen species (mROS) generation or HIF-1α protein stabilization (expression) Furthermore, the angiogenesis inhibitory activity may be evaluated by measuring cell migration or cell invasion. The test substances are as described above.

According to another aspect of the present invention, the present invention provides a method for screening a UQCRB activity inhibitor, the method comprising:

(a) establishing a mitochondrial ubiquinol-cytochrome c reductase binding protein (UQCRB) mutant animal cell line expressing a UQCRB mutant protein;

(b) contacting a test substance with the animal cells; and (c) analyzing the UQCRB inhibitory activity of the test substance.

In the method for screening a UQCRB activity inhibitor, step (c) may be performed by measuring the cell proliferative or angiogenic activity of the transfected cell line.

The method for screening a UQCRB activity inhibitor of the present invention is performed using the foregoing mitochondrial UQCRB mutant animal cell line of the present invention, and thus descriptions of overlapping contents therebetween are omitted to avoid excessive complication of the specification due to repetitive descriptions thereof. The test substances are as described above.

The UQCRB mutant cell line of the present invention induces angiogenesis through the mitochondrial reactive oxygen species (mROS)-mediated or HIF-1α-mediated mechanism. Furthermore, the UQCRB mutant cell line of the present invention induces structural abnormality or morphological abnormality (e.g., swelling), but does not affect cellular angiogenesis induction or cell proliferation.

Features and advantages of the present invention are summarized as follows:

(a) The present invention relates to a mitochondrial UQCRB mutant cell line expressing the UQCRB mutant protein.

(b) The present invention is directed to a novel research method for UQCRB activity evaluation using a novel mitochondrial UQCRB mutant cell line, and provides a method for anticancer activity evaluation, a method for angiogenesis inhibitory activity evaluation, and a method for screening a UQCRB activity inhibitor.

(c) In particular, the cell line of the present invention is a novel cell line having cell proliferative and angiogenesis inducing activities, and provides a method for screening an angiogenesis inhibitor or an anticancer material through the UQCRB activity inhibitory mechanism, and thus can be applied in the development of therapeutic agents against angiogenesis or mitochondria-mediated diseases and various cancers.

Figure 1A:
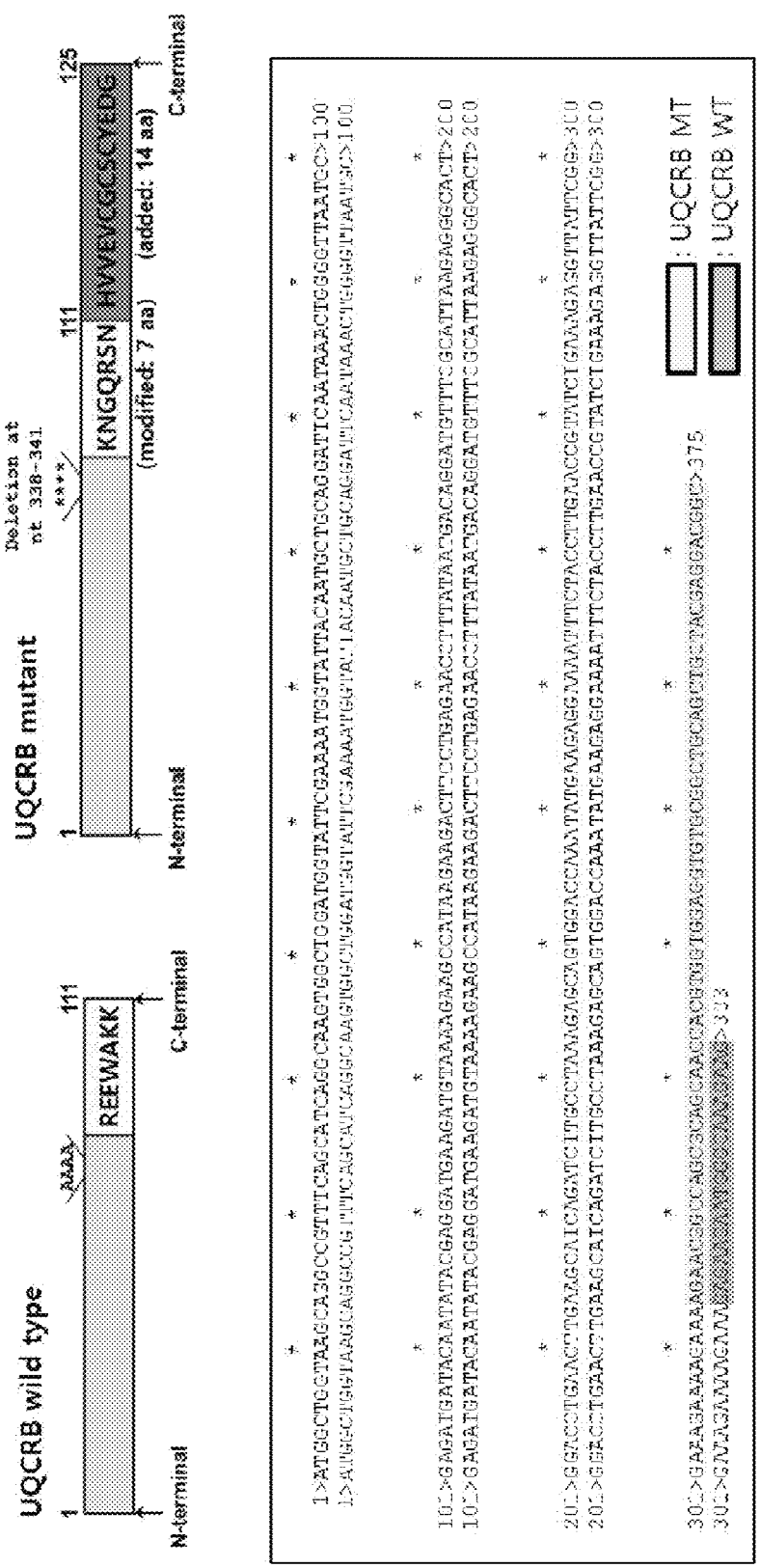
FIG. 1A-1C Generation and validation of UQCRB mutant stable cell lines. (1A) UQCRB mutant gene construct and its DNA sequence validation. Mutant sequences (SEQ ID NOs: 15 and 19) and wild-type sequences (SEQ ID NOs: 16, 17, and 18) are indicated. (1B) Expression level of mutant UQCRB and endogenous UQCRB as detected by RT-PCR. GAPDH served as an internal control. (1C) Mutant stable cell lines were validated by western blot by using anti-UQCRB and anti-Myc antibodies. Actin was used as an internal control.

Effect of a UQCRB mutation on HIF-1α and VEGF mRNA levels. (3C) Effect of a UQCRB mutation on HIF-1α protein stabilization and VEGF protein expression. (3D) Elevated level of secreted VEGF in the mutant stable cell lines.

FIG. 4A-4F Pro-angiogenic activity of UQCRB mutant stable cell lines and its regulation by UQCRB inhibitors. (4A) Pro-angiogenic activity of a UQCRB mutant through conditioned media (CM)-induced invasion of HUVECs. (4B) Effect of a UQCRB mutation on cell migration; black lines indicate the edge of the gap. (4C) Optical density levels of the colony formation assay by using UQCRB mutant stable cell lines or controls. (4D, 4E) Growth of the UQCRB mutant stable cell lines regulated by the UQCRB inhibitors terpestacin (T) and A1938 (A). Cells were treated with terpestacin (50 μM) or A1938 (10 μM) in a time-dependent manner. Cell growth was measured by the MTT colorimetric assay. (4F) Suppression of elevated mROS by terpestacin in UQCRB MT1 cells. mROS were measured using Mito-SOX™. Terpestacin (20 μM) was applied to UQCRB MT1 cells for 1 h; scale bars indicate 20 μm.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

Examples

Materials and Methods
Molecular Cloning

A full-length human UQCRB mutant expression vector was constructed by cloning a Polymerase Chain Reaction (PCR)-amplified full-length cDNA fragment of the UQCRB mutant (forward primer: 5'-ATGTGAATTCATGGCTGG-TAAGCAGGC-3' (SEQ ID NO: 4) and reverse primer: 5'-CTCGAGGCCGTCCTCGTAGCAGCTGCAGCCGCA-CACCTCCACCACGTG GTTGCTGCGCTGGCCGT-TCTTTTCTTTTCTTTCCCGAAT-3' (SEQ ID NO: 5)) into the EcoRI/XhoI site of pcDNA3.1/myc-His (Invitrogen, Grand Island, N.Y.). PCR was performed under the following conditions: initial denaturation for 5 min at 94° C., followed by 30 cycles of 1 min at 94° C., 1 min at 60° C., and 1 min at 72° C.

Generation of UQCRB Mutant Stable Cell Lines and Cell Culture

HEK293 cells were transfected with 1 μg UQCRB mutant expression vector by using the Lipofectamine™ LTX transfection reagent (Invitrogen, Grand Island, N.Y.), according to the manufacturer's instructions. To select mutant colonies, 1 mg/mL of G418 (Sigma-Aldrich, Saint Louis, Mo.) was applied for 2 weeks, and single-cell colonies were isolated using glass cylinders (Sigma-Aldrich, Saint Louis, Mo.). Control (HEK293) and mutant stable cell lines were grown in Dulbecco's modified Eagle's medium (DMEM; Invitrogen, Grand Island, N.Y.), supplemented with 10% fetal bovine serum (FBS; Invitrogen, Grand Island, N.Y.) and 1% antibiotics (Invitrogen, Grand Island, N.Y.). To maintain the mutant stable cell lines, 1 mg/mL G418 was applied steadily. All cells were incubated in a humidified incubator at 37° C., with a 5% CO2 level.

Transmission Electron Microscopy

Cells were harvested, washed once with PBS, and fixed with 2% paraformaldehyde/2% glutaraldehyde/0.5% CaCl2 for 6 h. After washing with 0.1 M phosphate buffer, followed by 1% OsO4 fixation, cells were dehydrated in 95% alcohol, incubated in propylene oxide for 10 min, kept in a 1:1 solution of EPON mixture and propylene oxide overnight, and embedded. Ultrathin sections were prepared with an LKB 8800 Ultratome III and were analyzed using a JEM-1011 JEOL transmission electron microscope.

Measurement of mROS Levels mROS levels were assessed by the red fluorescence mitochondrial superoxide indicator MitoSOX™ (Invitrogen, Grand Island, N.Y.). Cells were incubated with Mito-SOX (5 μM) and Hoechst 33342 (Life Technologies, Grand Island, N.Y.) for 10 min, washed once with phosphate buffered saline (PBS), and fixed with 4% formaldehyde. Results of MitoSOX™ and Hoechst staining were analyzed under a confocal microscope (Zeiss LSM 710; Carl Zeiss MicroImaging, Thornwood, N.Y.), and the fluorescence intensity of MitoSOX™ was measured by ImageJ.

Determination of ATP Levels

Cells were distributed into white 96-well plates and incubated for 24-72 h. ATP levels were determined using ATPlite™ (Perkin Elmer, Waltham, Mass.), according to the manufacturer's instructions.

Cell Proliferation Assay

Control and mutant stable cell lines were seeded onto 96-well plates and incubated for 24-72 h. Proliferation of the cells was measured using a 3-(4,5-dimethylthiazol-2-yl)-2, 5-diphenyltetrazolium bromide (MTT; Sigma-Aldrich, Saint Louis, Mo.) colorimetric assay.

RNA Isolation and Reverse Transcription-PCR (RT-PCR)

Total RNA was isolated using TRIzol (Invitrogen, Grand Island, N.Y.)-based methods. RT-PCR analysis was performed to validate the expression level of each mRNA by using specific primers (wild-type UQCRB, forward: 5'-AT-GTGAATTCATGGCTGGTAAGCAGGCC-3' (SEQ ID NO: 6), reverse: 5'-ATGCCTCGAGCTTCTTTGCCCAT-TCTTC-3' (SEQ ID NO: 7); HIF-1a, forward: 5'-GCTGGC-CCCAGCCGCTGGAG-3' (SEQ ID NO: 8), reverse: 5'-GAGTGCAGGGTCAGCACTAC-3' (SEQ ID NO: 9); VEGF, forward: 5'-ACCCATGGCAGAAGGAGGAG-3' (SEQ ID NO: 10), reverse: 5'-GACACCAGAGTCCGAC-CCGG-3' (SEQ ID NO: 11); and GAPDH (SEQ ID NO: 12), forward: 5'-AACAGCGACACCCACTCCTC-3' (SEQ ID NO: 13), reverse: 5'-GGAGGGGAGATTCAGTGTGGT-3' (SEQ ID NO: 14)). The expression level of the gene was quantified with Image Lab™ software (Bio-Rad, Hercules, Calif.).

Western Blot Analysis

Cell lysates were analyzed by 8%, 10%, and 12.5% sodium dodecyl sulfate polyacrylamide gel electrophoresis (SDS-PAGE) and then transferred to polyvinylidenedifluoride membranes (Millipore, Billerica, Mass.) by using standard methods. Blots were incubated with the following primary antibodies at 4° C. overnight: anti-UQCRB (Sigma-Aldrich, Saint Louis, Mo.), anti-Myc (Medical & Biological Laboratories Corp., Nagano, Japan), anti-HIF-1α (BD Bioscience, Bedford, Calif.), anti-VEGF (Abcam, Cambridge, Mass.), anti-tubulin (Millipore, Billerica, Mass.), and anti-actin (Abcam, Cambridge, Mass.). Immunolabeling was detected with an enhanced chemiluminescence (ECL) kit (GE Healthcare, Buckinghamshire, UK), according to the manufacturer's instructions. Images were quantified with Image Lab™ software (Bio-Rad, Hercules, Calif.).

Human VEGF Enzyme-Linked Immunosorbent Assay

UQCRB mutant stable cell lines and control cells (25×10⁴ cells) were seeded onto 6-well plates with 1 mL of medium and incubated at 37° C. for 24 h. The medium was collected, and the concentration of vascular endothelial growth factor (VEGF) protein in the supernatant was determined by a VEGF enzyme-linked immunosorbant assay (ELISA; R&D Systems, Minneapolis, Minn.), according to the manufacturer's instructions. The expression levels of the VEGF protein were normalized relative to that of the control samples.

In Vitro Invasion Assay

Pro-angiogenic activity of UQCRB mutant stable cells was tested by applying the supernatants of the cells to human umbilical vascular endothelial cells (HUVECs) by using a Transwell chamber system with polycarbonate filter inserts of 8.0 μm pore size (Corning Costar, Cambridge, Mass.). HUVECs were grown for 7-10 passages in EBM-2 medium (Cambrex Bio Science, Baltimore, Md.), supplemented with 10% FBS. The total number of invading cells was counted using a microscope (IX71; Olympus America Inc., Center Valley, Pa.) at 100× magnification.

Cell Migration Assay

Cells were seeded at a high density onto 6-well plates, and a scratch was made in the middle of the well by using a sterilized micropipette tip to create a gap of constant width. After 17 h of incubation in DMEM, the migration of cells was analyzed using a microscope.

Colony Formation Assay

Cells (5×102) were seeded onto 6-well plates and incubated for 2 weeks until colonies were formed. Cells were fixed with 4% formaldehyde, stained with 0.25% crystal violet for 10 min, and washed with double-distilled water. Stained cells were treated with 70% methanol before colorimetric measurement.

Statistical Analysis

Results are expressed as mean±standard deviation (SD). All data are representative of at least three independent assays.

Results

UQCRB Mutant Stable Cell Lines were Established Based on a Human Case Report

Figure 1B:
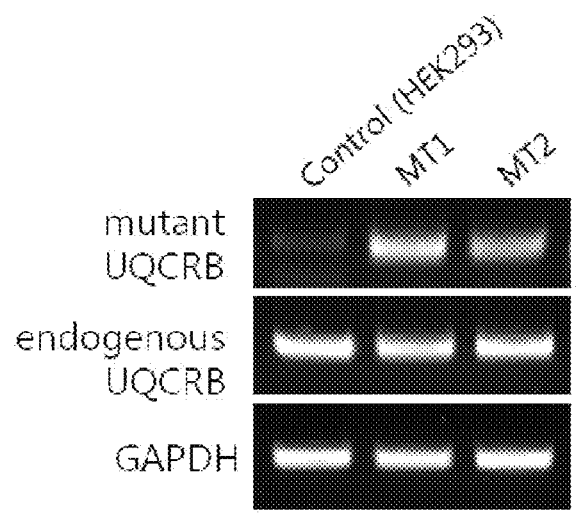
Figure 1C:
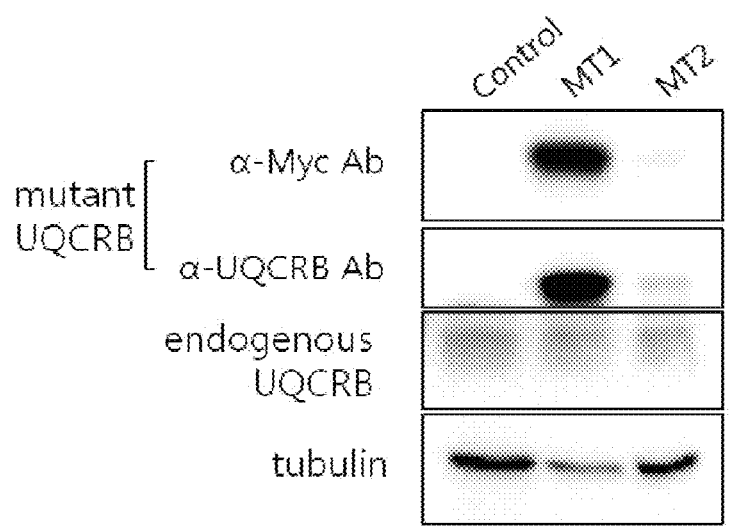

To investigate the biological function of UQCRB, we referred to a UQCRB mutant identified previously in human cDNA [12]. This mutant was cloned with a 4-bp deletion at nucleotides 338-341 of the UQCRB gene, based on the human case report, and subcloned for protein expression in mammalian cells. The resultant UQCRB mutant protein had alterations in seven amino acid residues and an additional stretch of 14 amino acids at the C-terminal end (FIG. 1A). The sequence of the gene construct was validated by DNA sequencing before transfection into HEK293 cells. After single-cell colony selection, two UQCRB mutant stable cell lines, comprising the same mutation but different expression levels, were named MT1 and MT2 and were analyzed at the mRNA and protein levels (FIG. 1B,C). MT1 showed a high expression level of the mutant protein, while MT2 exhibited a relatively low expression level of the mutant protein. The cell lines did not differ in their wild-type UQCRB protein expression levels.

Figure 2A:
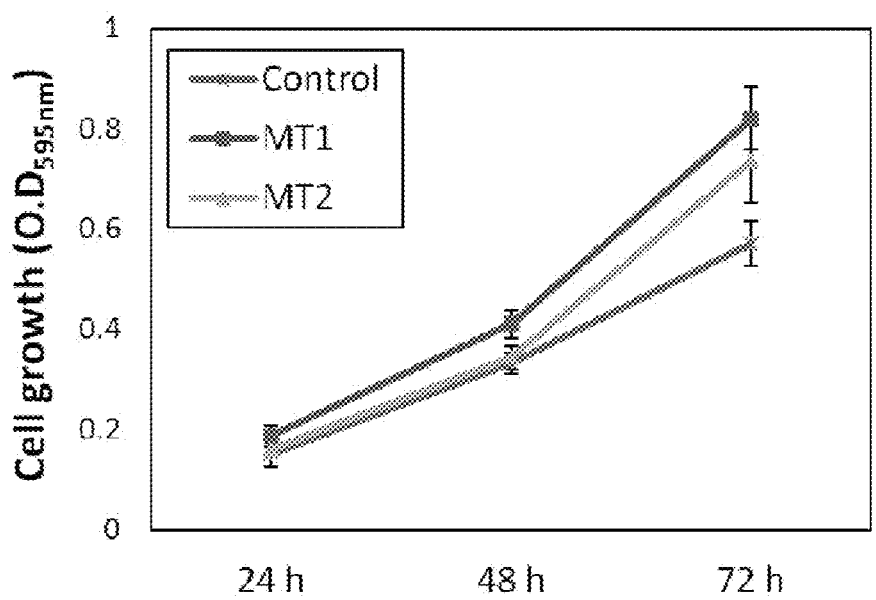
FIG. 2A-2C Effect of a UQCRB mutation on cell proliferation and mitochondrial morphology. (2A) Proliferative activity of a UQCRB mutant as determined by MTT colorimetric assay in a time-dependent manner. (2B) ATP levels were quantified in a time-dependent manner. (2C) Mitochondrial morphology of cells. Swollen mitochondria were examined compared to controls. Scale bars indicate 2000 nm and 500 nm for images of magnification 20000× and 50000×, respectively.
Figure 2B:
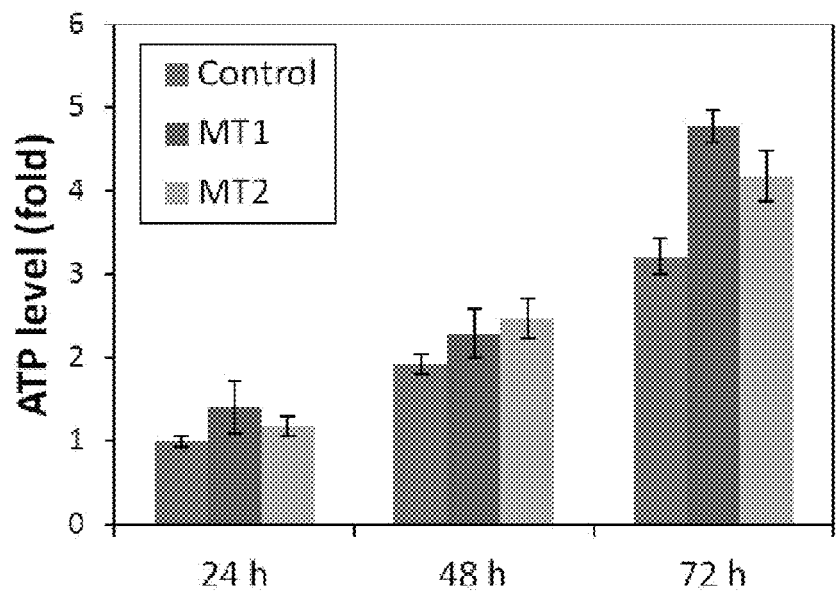
Figure 2C:
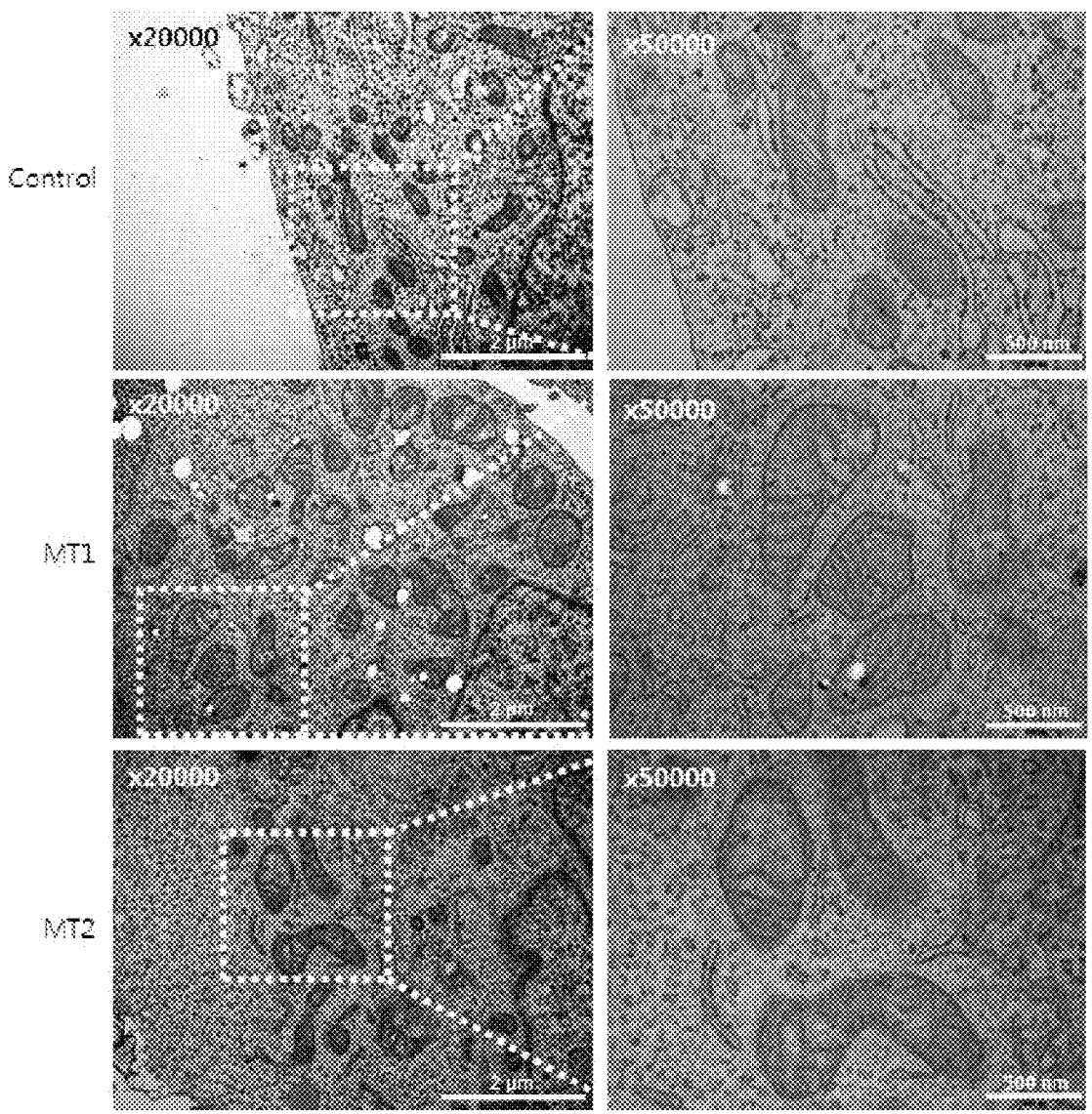

UQCRB Mutant Stable Cell Lines Exhibited Proliferative Activity, Regardless of Mitochondrial Abnormalities To characterize the UQCRB mutant stable cell lines MT1 and MT2, cell proliferation was first measured using the MTT colorimetric assay. Surprisingly, compared to controls, MT1 exhibited significantly increased growth in a time-dependent manner (FIG. 2A). The growth of MT2 was weaker than that of MT1 but stronger than that of controls. Furthermore, both UQCRB mutant cell lines showed increased ATP levels (FIG. 2B). Notably, mitochondrial morphology of MT1 and MT2 cells showed structural abnormalities characterized by remarkable swelling (FIG. 2C).

UQCRB Mutant Stable Cell Lines Induced mROS-Mediated HIF1 Signal Transduction

Figure 3A:
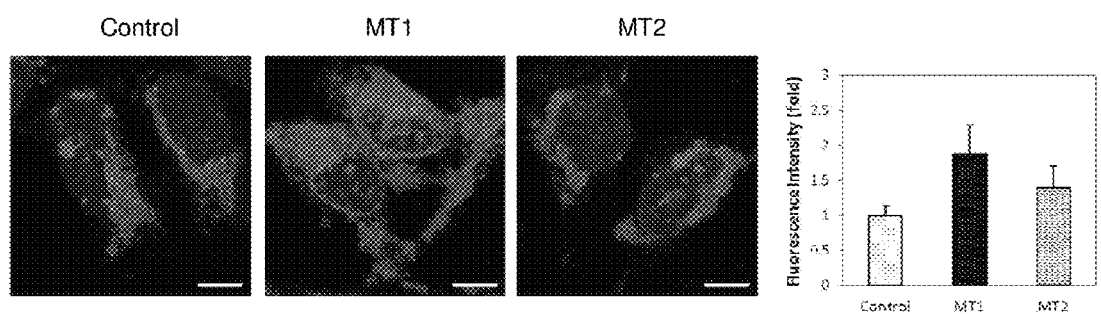
FIG. 3A-3D Induction of VEGF expression through mROS-mediated HIF-1α expression. (3A) mROS levels determined by MitoSOX™; scale bars indicate 10 μm. (3B)
Figure 3B:
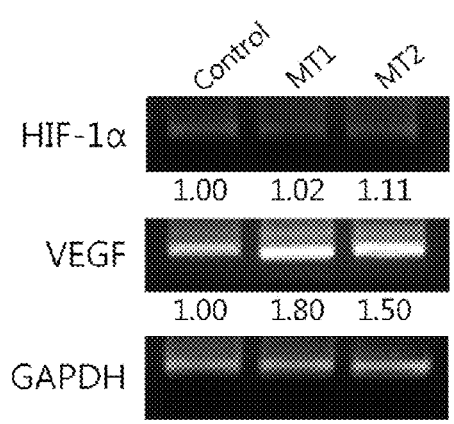
Figure 3C:
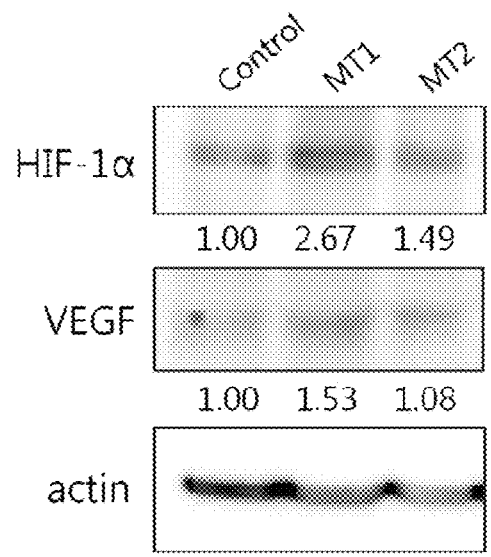
Figure 3D:
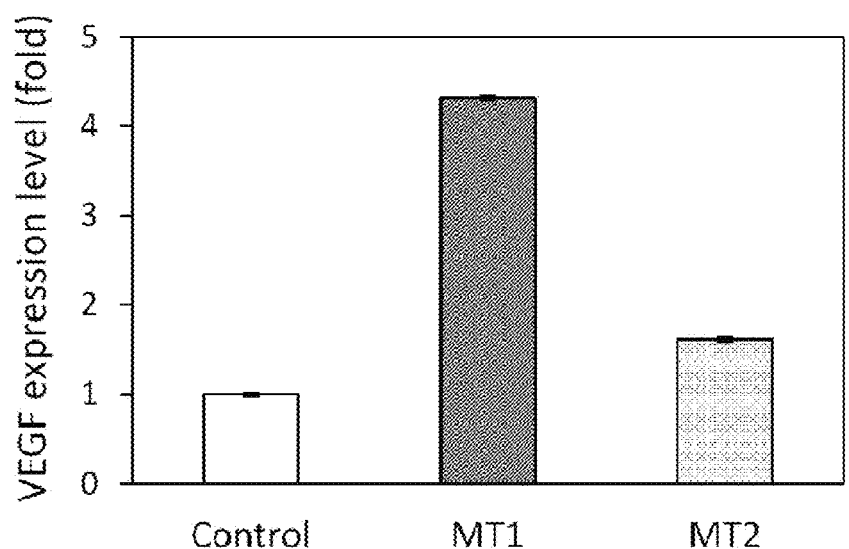

Previously, Jung et al. suggested that UQCRB might play an important role in the oxygen-sensing mechanism by modulating mROS- and HIF-mediated angiogenesis under hypoxic conditions [6]. Thus, we examined mROS generation in MT1 and MT2 cells by using the mROS-specific red fluorescence indicator MitoSOX™. Notably, mROS generation was increased in both mutant cell lines compared to controls (FIG. 3A). Previous studies indicated that elevated mROS generation is essential for increased HIF-1α stability [13]. To test whether increased mROS generation could affect HIF-1α stability, we examined the HIF-1α protein level by western blot. As expected, HIF-1α protein, but not mRNA, was stabilized in MT1 and MT2 cells (FIG. 3B, C). Likewise, an increased expression of the VEGF gene[14, 15], downstream of HIF-1α, was observed in MT1 and MT2 cells by western blot and RT-PCR (FIG. 3B, C). The secretion level of VEGF was measured by human VEGF ELISA. Compared to controls, MT1 showed a more than 4-fold increase of VEGF expression (FIG. 3D). These results indicated that UQCRB mutant stable cell lines significantly induced VEGF expression through mROS-mediated HIF-1α signal transduction.

The Pro-Angiogenic Effect of UQCRB Mutation is Regulated by UQCRB Inhibitors

Figure 4A:
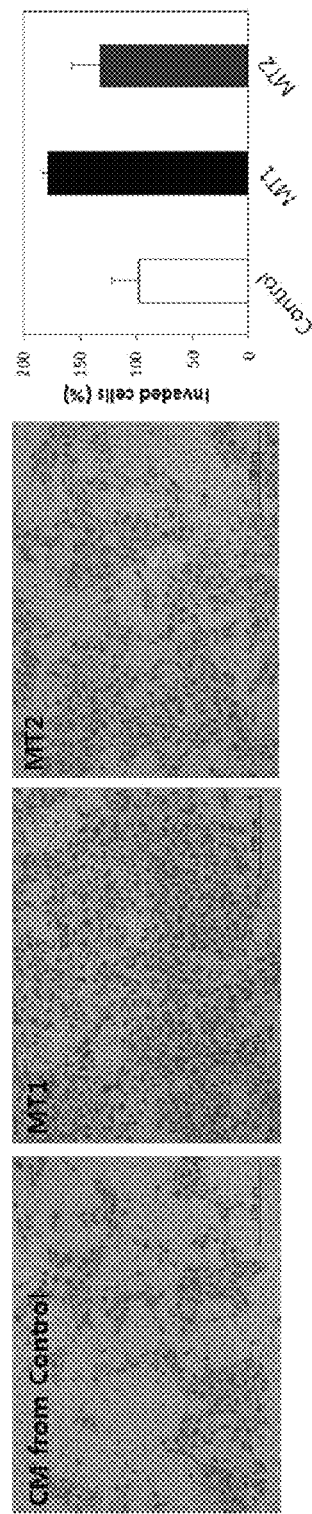
Figure 4B:
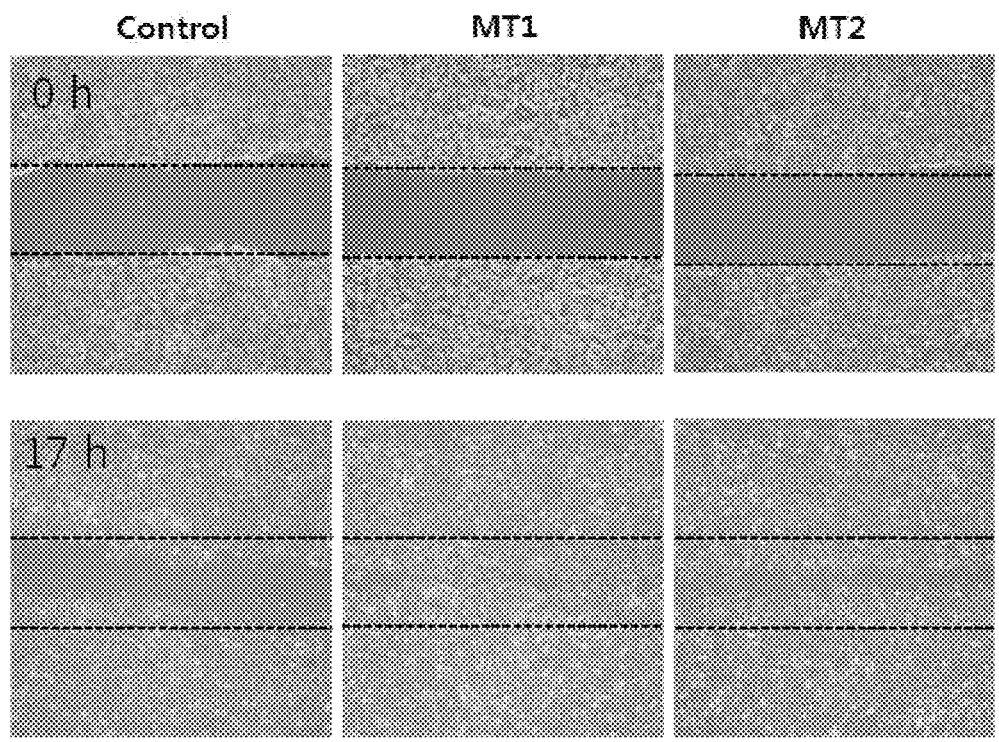
Figure 4C:
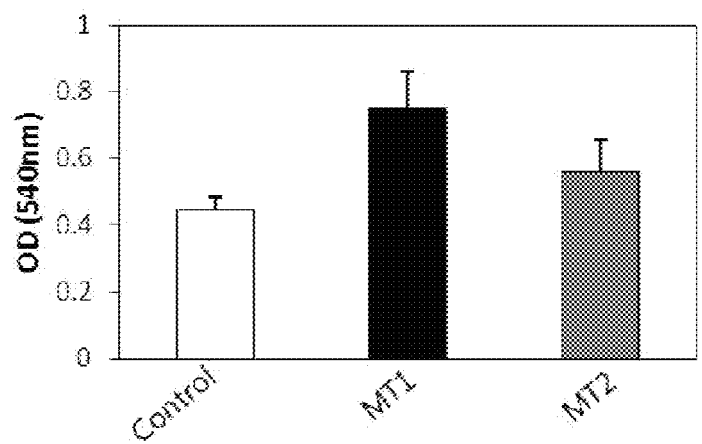

Since VEGF is one of the critical cytokines in angiogenesis signaling, we confirmed the pro-angiogenic activities of MT1 and MT2 cells by various in vitro angiogenesis assays. First, HUVECs were treated with conditioned media, derived from MT1 and MT2, which were added to the lower chamber and incubated for 16 h. In accordance with an increased VEGF expression, the invasive activity was also significantly enhanced in HUVECs in contrast to controls (FIG. 4A). Next, cell migration of MT1 and MT2 was investigated. Compared to controls, both cell lines exhibited remarkable cell migration within 17 h (FIG. 4B). Furthermore, in the colony formation assay, MT1 and MT2 showed increased colony formation relative to that shown by controls (FIG. 4C). These data indicate that compared to controls, MT1 and MT2 have remarkably high pro-angiogenic activities.

Figure 4D:
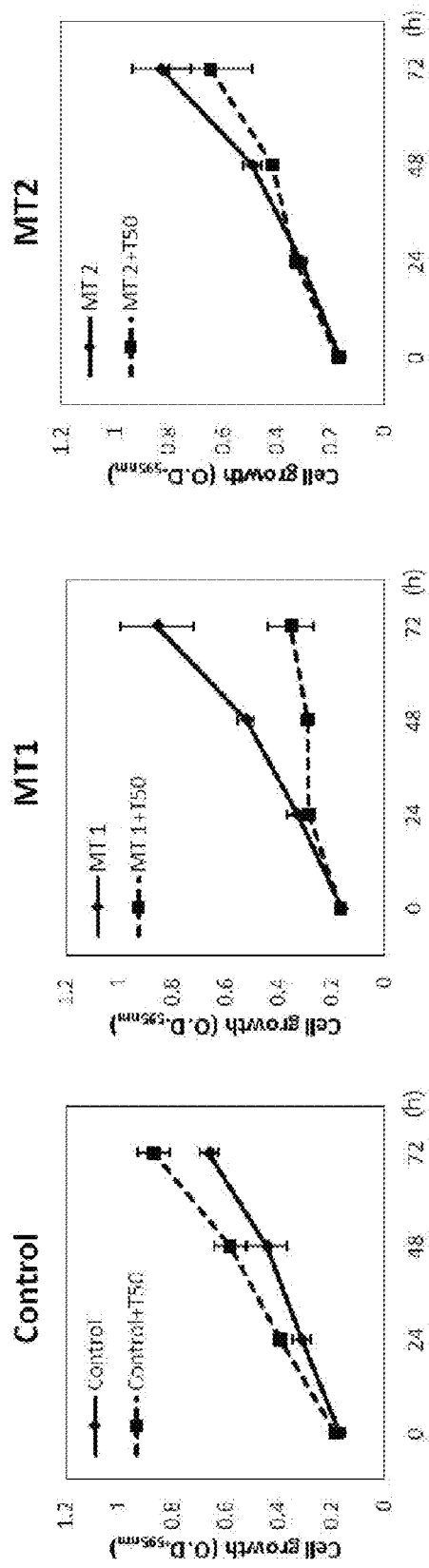
Figure 4E:
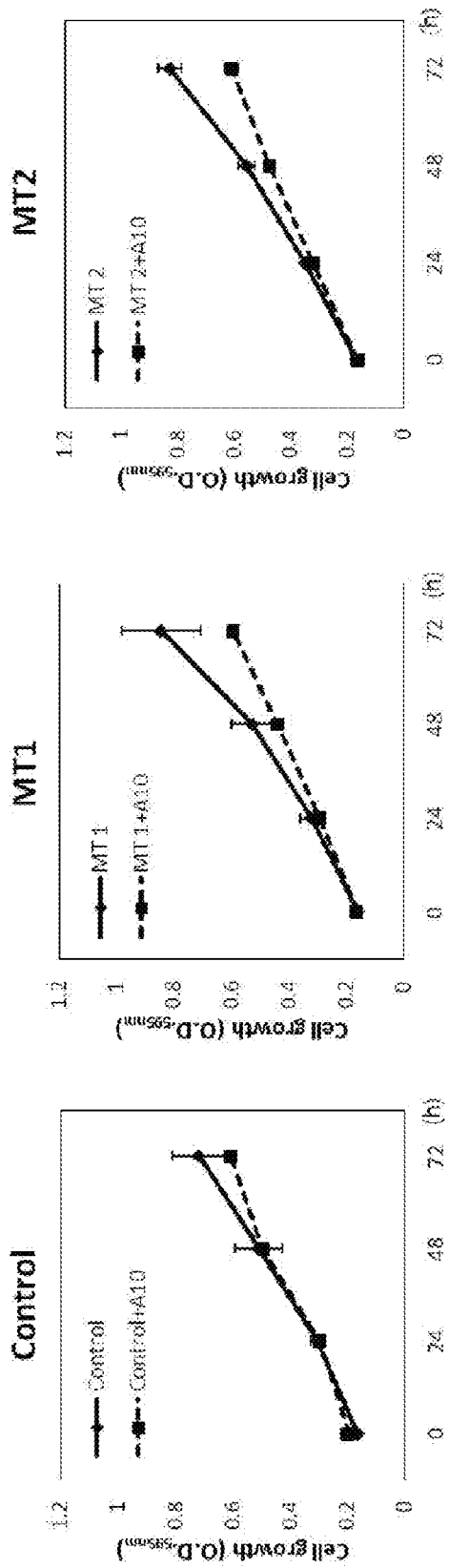
Figure 4F:
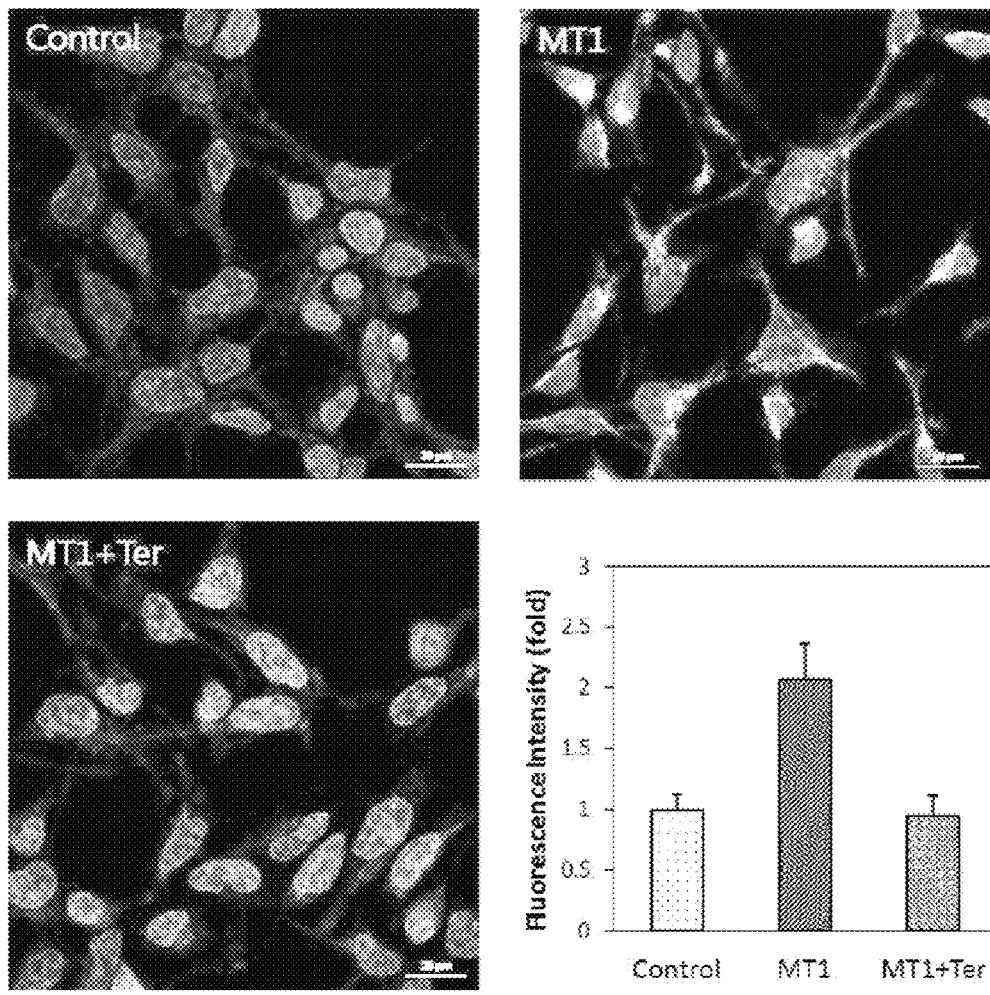

Since UQCRB is a molecular target of the natural compound terpestacin [6], we examined the effect of terpestacin on UQCRB mutant stable cell lines. To test whether terpestacin affects MT1 and MT2, cell growth was measured with or without terpestacin for 3 days. Interestingly, terpestacin remarkably inhibited proliferation of MT1 and MT2 at a concentration of 50 μM, which did not affect the proliferation of controls (FIG. 4D). In addition, we tested the effect of A1938, a potent synthetic UQCRB inhibitor [16], on the proliferation of MT1 and MT2. As shown in FIG. 4E, compared to controls, MT1 and MT2 showed sensitivity to A1938 at a concentration of 10 μM. Notably, terpestacin treatment attenuated mROS induction in MT1 to a basal level (FIG. 4F). Overall, these results demonstrate that the proliferative and pro-angiogenic activities of MT1 and MT2 can be regulated by UQCRB inhibitors.

Discussion

The mitochondrion is not only an important powerhouse of the cell owing to its ability to produce majority of the ATP [17], but is also an integral member of the cell's oxygen-sensing machinery [13]. Among the five mitochondrial electron transfer chain complexes, complex III is the most well-known site of ROS generation. Recently, UQCRB, one of the subunits of complex III, was described as an oxygen sensor in hypoxia-induced [6] and VEGF-induced [7] angiogenesis. In addition, functional inhibition of UQCRB by gene knock-down inhibited angiogenesis in zebrafish [18]. Yet, the biological role of UQCRB is still elusive in respect with its pathological effects. Therefore, we generated UQCRB mutant stable cell lines based on a previous human case report. Two mutant stable cell lines, MT1 and MT2, showed outstanding cell growth and pro-angiogenic activities, together with morphological abnormalities in mitochondria. We further demonstrated that the mROS-induced HIF-1α signaling pathway, which resulted in VEGF induction, could contribute to pro-angiogenic activities of MT1 and MT2. Meanwhile, the correlation between cell proliferation and mitochondrial morphological abnormalities of MT1 and MT2 needs to be investigated in the following studies. Mitochondrial alteration has long been proposed to play an important role in tumorigenesis [19,20]. Baysal et al. demonstrated how mutations in the mitochondrial complex II gene SDHD could contribute to tumor formation [21]. This proposed redox stress mechanism with increased mROS generation in mitochondria, resulting in pseudohypoxia, would be consistent with our results, linking mitochondrial abnormality to angiogenesis-related disease and cancer [22]. Interestingly, we demonstrated that the proliferation of MT1 and MT2 could be regulated by the UQCRB inhibitors terpestacin and A1938. It is conceivable that inhibition of mROS by UQCRB inhibitors could affect cell growth.

In summary, our results propose a molecular basis for UQCRB mutant-related biological processes. In addition, this study contributes to our understanding of the link between mitochondrial abnormalities caused by mutations in UQCRB and angiogenesis- or mitochondria-related diseases. Furthermore, these results point to options for correcting the pathological effects of UQCRB mutations by UQCRB inhibitors.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

REFERENCES

[1] J. Nunnari, A. Suomalainen, Mitochondria: in sickness and in health, Cell 148 (2012) 1145-1159.
[2] D. C. Wallace, Mitochondria and cancer, Nat Rev Cancer 12 (2012) 685-698.
[3] P. Dromparis, E. D. Michelakis, Mitochondria in vascular health and disease, Annu Rev Physiol 75 (2013) 95-126.
[4] K. F. Petersen, S. Dufour, D. Befroy, R. Garcia, G. I. Shulman, Impaired mitochondrial activity in the insulin-resistant offspring of patients with type 2 diabetes, N Engl J Med 350 (2004) 664-671.
[5] H. Suzuki, Y. Hosokawa, H. Toda, M. Nishikimi, T. Ozawa, Cloning and sequencing of a cDNA for human mitochondrial ubiquinone-binding protein of complex III, Biochem Biophys Res Commun 156 (1988) 987-994.
[6] H. J. Jung, J. S. Shim, J. Lee, Y. M. Song, K. C. Park, S. H. Choi, N. D. Kim, J. H. Yoon, P. T. Mungai, P. T. Schumacker, H. J. Kwon, Terpestacin inhibits tumor angiogenesis by targeting UQCRB of mitochondrial complex III and suppressing hypoxia-induced reactive oxygen species production and cellular oxygen sensing, J Biol Chem 285 (2010) 11584-11595.
[7] H. J. Jung, Y. Kim, J. Chang, S. W. Kang, J. H. Kim, H. J. Kwon, Mitochondrial UQCRB regulates VEGFR2 signaling in endothelial cells, J Mol Med (Berl) 91 (2013) 1117-1128.
[8] H. L. Jia, Q. H. Ye, L. X. Qin, A. Budhu, M. Forgues, Y. Chen, Y. K. Liu, H. C. Sun, L. Wang, H. Z. Lu, F. Shen, Z. Y. Tang, X. W. Wang, Gene expression profiling reveals potential biomarkers of human hepatocellular carcinoma, Clin Cancer Res 13 (2007) 1133-1139.
[9] K. O. Wrzeszczynski, V. Varadan, J. Byrnes, E. Lum, S. Kamalakaran, D. A. Levine, N. Dimitrova, M. Q. Zhang, R. Lucito, Identification of tumor suppressors and oncogenes from genomic and epigenetic features in ovarian cancer, PLoS One 6 (2011) e28503.
[10] T. Harada, C. Chelala, T. Crnogorac-Jurcevic, N. R. Lemoine, Genome-wide analysis of pancreatic cancer using microarray-based techniques, Pancreatology 9 (2009) 13-24.
[11] J. Lascorz, M. Bevier, W. V. Schonfels, H. Kalthoff, H. Aselmann, J. Beckmann, J. Egberts, S. Buch, T. Becker, S. Schreiber, J. Hampe, K. Hemminki, A. Forsti, C. Schafmayer, Polymorphisms in the mitochondrial oxidative phosphorylation chain genes as prognostic markers for colorectal cancer, BMC Med Genet 13 (2012) 31.
[12] S. Haut, M. Brivet, G. Touati, P. Rustin, S. Lebon, A. Garcia-Cazorla, J. M. Saudubray, A. Boutron, A. Legrand, A. Slama, A deletion in the human QP-C gene causes a complex III deficiency resulting in hypoglycaemia and lactic acidosis, Hum Genet 113 (2003) 118-122.
[13] T. Klimova, N. S. Chandel, Mitochondrial complex III regulates hypoxic activation of HIF, Cell Death Differ 15 (2008) 660-666.
[14] D. E. Richard, E. Berra, J. Pouyssegur, Angiogenesis: how a tumor adapts to hypoxia, Biochem Biophys Res Commun 266 (1999) 718-722.
[15] J. A. Forsythe, B. H. Jiang, N. V. Iyer, F. Agani, S. W. Leung, R. D. Koos, G. L. Semenza, Activation of vascular endothelial growth factor gene transcription by hypoxia-inducible factor 1, Mol Cell Biol 16 (1996) 4604-4613.
[16] H. J. Jung, K. H. Kim, N. D. Kim, G. Han, H. J. Kwon, Identification of a novel small molecule targeting UQCRB of mitochondrial complex III and its anti-angiogenic activity, Bioorg Med Chem Lett 21 (2011) 1052-1056.
[17] C. Desler, L. J. Rasmussen, Mitochondria in biology and medicine—2012, Mitochondrion 16 (2014) 2-6.
[18] Y. S. Cho, H. J. Jung, S. H. Seok, A. Y. Payumo, J. K. Chen, H. J. Kwon, Functional inhibition of UQCRB suppresses angiogenesis in zebrafish, Biochem Biophys Res Commun 433 (2013) 396-400.
[19] J. S. Park, L. K. Sharma, H. Li, R. Xiang, D. Holstein, J. Wu, J. Lechleiter, S. L. Naylor, J. J. Deng, J. Lu, Y. Bai, A heteroplasmic, not homoplasmic, mitochondrial DNA mutation promotes tumorigenesis via alteration in reactive oxygen species generation and apoptosis, Hum Mol Genet 18 (2009) 1578-1589.
[20] S. Ohsawa, Y. Sato, M. Enomoto, M. Nakamura, A. Betsumiya, T. Igaki, Mitochondrial defect drives non-autonomous tumour progression through Hippo signalling in *Drosophila*, Nature 490 (2012) 547-551.
[21] B. E. Baysal, R. E. Ferrell, J. E. Willett-Brozick, E. C. Lawrence, D. Myssiorek, A. Bosch, A. van der Mey, P. E. Taschner, W. S. Rubinstein, E. N. Myers, C. W. Richard, 3rd, C. J. Cornelisse, P. Devilee, B. Devlin, Mutations in SDHD, a mitochondrial complex II gene, in hereditary paraganglioma, Science 287 (2000) 848-851.
[22] E. Gottlieb, I. P. Tomlinson, Mitochondrial tumour suppressors: a genetic and biochemical update, Nat Rev Cancer 5 (2005) 857-866.

What is claimed is:

1. A method for anticancer activity evaluation, the method comprising:
(a) establishing a mitochondrial ubiquinol-cytochrome c reductase binding protein (UQCRB) mutant animal cell line expressing a UQCRB mutant protein, wherein the mitochondrial UQCRB mutant animal cell line is transfected with a vector including a nucleotide sequence coding human ubiquinol-cytochrome c reductase binding protein (UQCRB) mutant of SEQ ID NO: 1, to express the human UQCRB mutant protein;
(b) contacting a test substance with the animal cells; and
(c) analyzing the anticancer activity of the test substance.

2. The method of claim 1, wherein the anticancer activity is evaluated by analyzing the UQCRB inhibitory activity of the test substance.

3. A method for angiogenesis inhibitory activity evaluation, the method comprising:
(a) establishing a mitochondrial ubiquinol-cytochrome c reductase binding protein (UQCRB) mutant animal cell line expressing a UQCRB mutant protein, wherein the mitochondrial UQCRB mutant animal cell line is transfected with a vector including a nucleotide sequence coding human ubiquinol-cytochrome c reductase binding protein (UQCRB) mutant of SEQ ID NO: 1, to express the human UQCRB mutant protein;
(b) contacting a test substance with the animal cells; and
(c) analyzing the angiogenesis inhibitory activity of the test substance.

4. The method of claim 3, wherein the angiogenesis inhibitory activity is evaluated by analyzing the UQCRB inhibitory activity of the test substance.

5. The method of claim 3, wherein in step (c), the angiogenesis inhibitory activity is evaluated by measuring mitochondrial reactive oxygen species (mROS)-mediated or HIF-1α-mediated angiogenic activity.

6. A method for screening a UQCRB activity inhibitor, the method comprising:
(a) establishing a mitochondrial ubiquinol-cytochrome c reductase binding protein (UQCRB) mutant animal cell line expressing a UQCRB mutant protein, wherein the mitochondrial UQCRB mutant animal cell line is transfected with a vector including a nucleotide sequence coding human ubiquinol-cytochrome c reductase binding protein (UQCRB) mutant of SEQ ID NO: 1, to express the human UQCRB mutant protein;
(b) contacting a test substance with the animal cells; and
(c) analyzing the UQCRB inhibitory activity of the test substance.

7. The method of claim 6, wherein step (c) is performed by measuring cell proliferative or angiogenic activity of the cells.

* * * * *